United States Patent [19]

Sinofsky et al.

[11] Patent Number: 5,254,112

[45] Date of Patent: Oct. 19, 1993

[54] DEVICE FOR USE IN LASER ANGIOPLASTY

[75] Inventors: Edward Sinofsky, Peabody; W. Scott Andrus, Lexington; Michael Madden, Ashby, all of Mass.

[73] Assignee: C. R. Bard, Inc., Murray Hill, N.J.

[21] Appl. No.: 604,931

[22] Filed: Oct. 29, 1990

[51] Int. Cl.$^5$ .......................... A61N 5/06; A61B 8/12
[52] U.S. Cl. ........................................... 606/7; 606/10; 606/12; 606/15; 606/17; 128/660.01; 128/660.03; 128/662.03; 128/662.06
[58] Field of Search ...................... 128/660.01, 660.03, 128/662.03, 662.06, 395, 397, 398; 606/7, 10-18

[56] References Cited

U.S. PATENT DOCUMENTS

| | | | |
|---|---|---|---|
| 3,532,181 | 10/1970 | DeMarie et al. | 181/0.5 |
| 4,086,484 | 4/1978 | Steensma | 250/199 |
| 4,169,662 | 10/1979 | Kaule et al. | 350/358 |
| 4,405,198 | 9/1983 | Taylor | 350/96.29 |
| 4,530,078 | 7/1985 | Lagakos et al. | 367/149 |
| 4,558,706 | 12/1985 | Nakada et al. | 128/660 |
| 4,576,177 | 3/1986 | Webster, Jr. | 128/660 |
| 4,587,972 | 5/1986 | Morantte, Jr. | 128/660 |
| 4,637,401 | 1/1987 | Johnston | 128/663 |
| 4,641,650 | 2/1987 | Mok | 128/303.1 |
| 4,665,925 | 5/1987 | Millar | 128/663 |
| 4,666,308 | 5/1987 | Williams | 356/432 |
| 4,726,651 | 2/1988 | Wei et al. | 350/96.29 |
| 4,730,093 | 3/1988 | Mehta et al. | 219/121.63 |
| 4,759,613 | 7/1988 | Fox | 350/358 |
| 4,785,806 | 11/1988 | Deckelbaum | 128/303.1 |
| 4,794,931 | 1/1989 | Yock | 128/660.03 |
| 4,841,977 | 6/1989 | Griffith et al. | 128/660.03 |
| 4,844,585 | 7/1989 | Culshaw et al. | 350/96.29 |
| 4,932,954 | 6/1990 | Wondrazek et al. | 606/128 |
| 5,041,121 | 8/1991 | Wondrazek et al. | 606/15 |

FOREIGN PATENT DOCUMENTS

| | | |
|---|---|---|
| 3506249A1 | 2/1985 | Fed. Rep. of Germany . |
| 3600713A1 | 1/1986 | Fed. Rep. of Germany . |
| 3736953A1 | 10/1987 | Fed. Rep. of Germany . |
| WO89/04143 | 5/1989 | PCT Int'l Appl. . |

OTHER PUBLICATIONS

R. C. Addison, Jr. et al. "Synthesis of an Ultrasonic Array Using Laser-Based Techniques," *1987 Ultrasonics Symp.*, pp. 1109-1113.

H. M. Ledbetter et al. "Laser Induced Rayleigh Waved in Aluminum," *J. Acoust. Soc. Am.*, vol. 65, No. 3, Mar. 1979, pp. 840-842.

J. A. Vogel et al., "Beam Steering of Laser Gnerated Ultrasound," *Ultrasonics International 87 Conf. Proc.*, pp. 141-152.

L. S. Gournay, "Conversion of Electromagnetic To Acoustic Energy by Surface Heating," *J. Acoust. Soc. Am.*, vol. 40, No. 6, 1966, pp. 1322-1330.

O. B. Ovchinnikov et al., "Recording of the Space-- Time Characteristics of Short Acoustic Pulses Generated by Optical Irradiation," *Sov. Phys. Acoust.*, vol. 33, No. 2, Mar.-Apr. 1987, pp. 182-184.

Scruby, "Some Applications of Laser Ultrasound," *Ultrasonics*, Jul. 1989, vol. 27.

Wang et al., "$CO_2$ Laser-Generated Acoustic Wave in Aluminum," *J. App. Phys.*, Jul. 1, 1989, vol. 66.

*Primary Examiner*—David M. Shay
*Attorney, Agent, or Firm*—Darby & Darby

[57] ABSTRACT

Apparatus for use in removing atherosclerotic plaque deposits in a blood vessel comprises a high power laser, an elongated, flexible catheter adapted to be inserted into and advanced through the blood vessel, a plurality of circumferentially arrayed optical fibers extending axially through the catheter, and an ultrasonic transducer at the distal end of the catheter for transmitting acoustical energy toward a selected area of the inner surface of a blood vessel in response to laser energy coupled through any one of the optical fibers and impinging upon the transducer. A detector proximal of the ultrasonic transducer is responsive to ultrasonic energy reflected from the blood vessel and produces a signal indicative of the tissue interfaces of the blood vessel. Laser energy can be transmitted from the high power laser through the same optical fiber used for the diagnostic procedure to ablate plaque in the blood vessel.

20 Claims, 2 Drawing Sheets

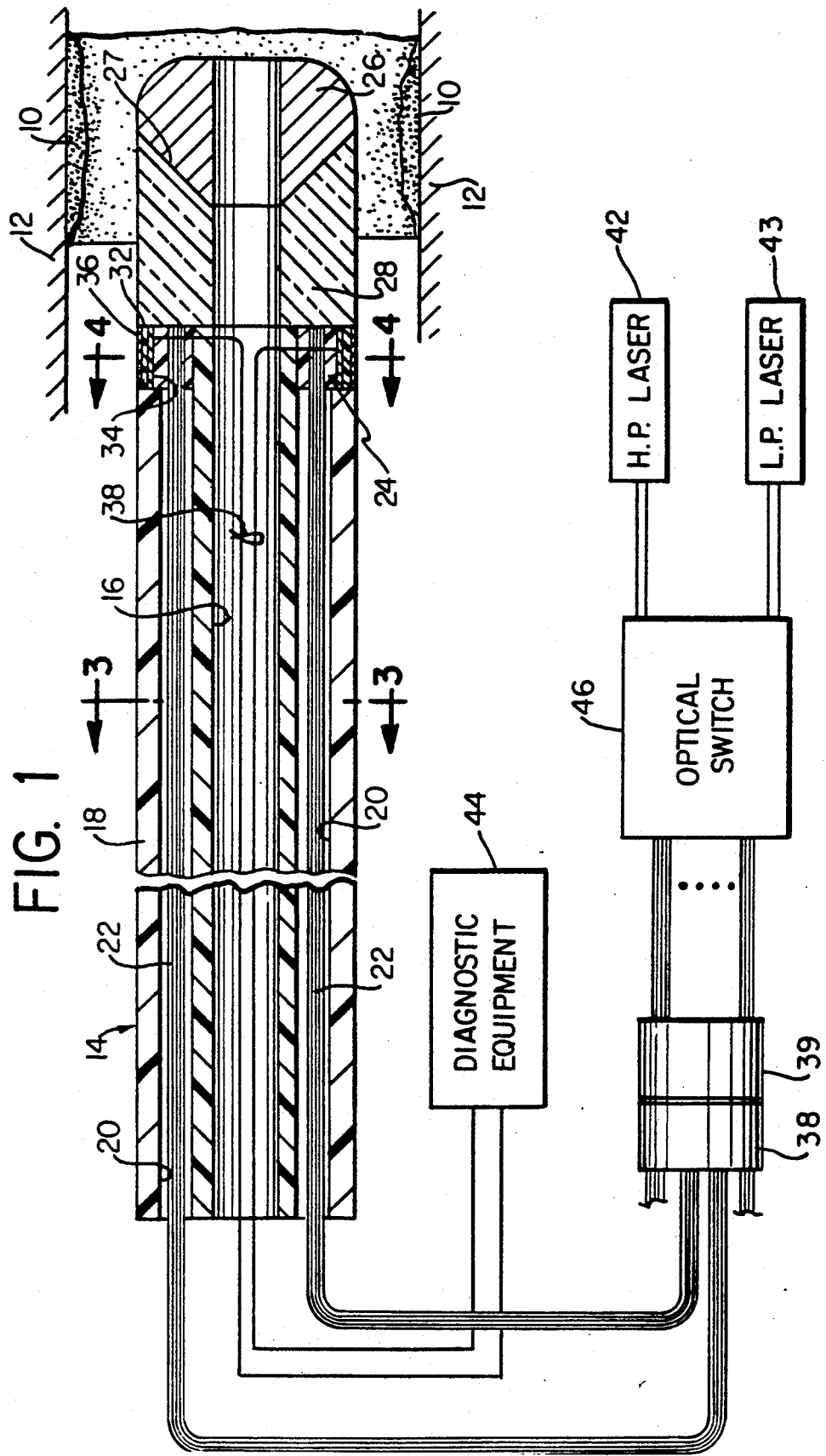

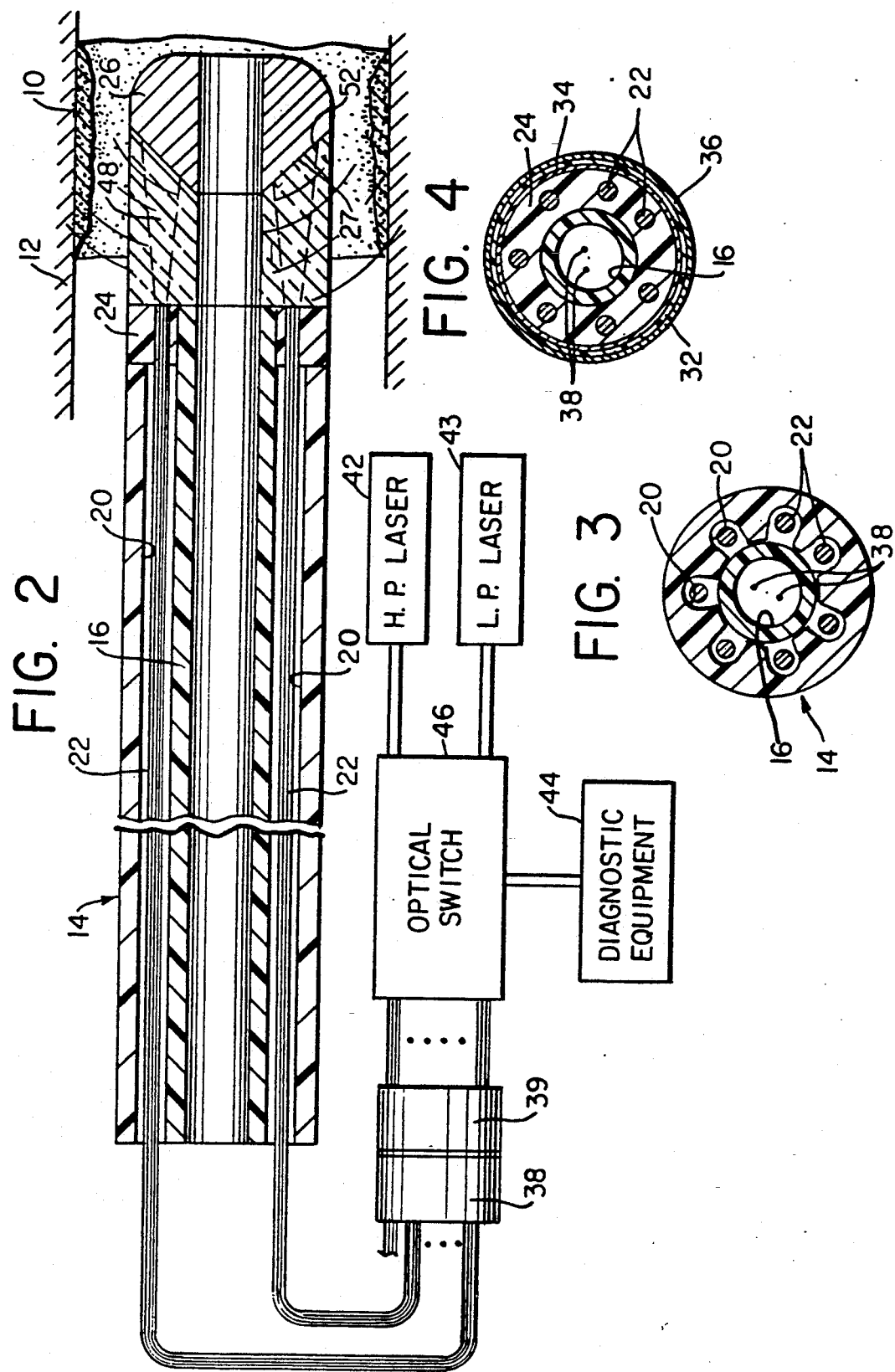

DEVICE FOR USE IN LASER ANGIOPLASTY

This invention relates to the laser ablation of human tissue.

BACKGROUND OF THE INVENTION

Atherosclerotic plaque deposits tend to occlude and thus restrict the f low of blood in coronary arteries. Such deposits are a major cause of heart disease and various techniques have been proposed to remove atherosclerotic plaque without requiring surgery.

The use of lasers for the purpose of evaporating (ablating) atherosclerotic plaque deposits has been proposed and is currently under investigation by a number of researchers. The procedure (known as angioplasty) involves delivery of laser energy through an optical fiber to the site at which ablation must occur. While laser angioplasty is potentially advantageous, it has proven difficult to control accurately and reliably the process so as to ensure that only atherosclerotic plaque is ablated. Accidental perforation of an artery during a laser ablation process can be fatal.

A variety of techniques have been proposed to position accurately the tip of the optical fiber through which the laser energy is transmitted with respect to the plaque that it is desired to ablate. Among other things, accurate positioning of the optical fiber requires diagnostic procedures for determining the presence of plaque deposits and the proper positioning of the end of the fiber with respect to such deposits so that only that portion of the tissue diagnosed as plaque will be ablated by the high power laser energy. See, for example, Deckelbaum U.S. Pat. No. 4,785,806, and Mok U.S. Pat. No. 4,641,650. If only plaque deposits are subjected to the high energy laser, the likelihood of accidental perforation of the artery is reduced.

Ultrasonic diagnosis has been proposed also to avoid possible perforation of an arterial wall during laser angioplasty. In such systems, ultrasonic pulses are transmitted toward the arterial wall and the time of arrival of the echoes from the tissue interfaces measured. Knowing the velocity of sound, the distance (range) of each tissue layer from the catheter can be calculated to provide a visual image of the cross-section of the arterial wall scanned by the ultrasound. The image reflects the thickness of the arterial wall so that the operator knows not to ablate tissue where the arterial wall is dangerously thin. Secondarily, particularly in the hands of a skilled operator, the cross-sectional image can be used to help distinguish plaque deposits from arterial tissues to ensure that the high energy laser ablation pulses are directed only at the atherosclerotic tissue.

The main object of the present invention is to provide an improved catheter construction for use in laser angioplasty wherein the elements required for delivery of the energy used for range sensing and ablation are contained within the catheter.

A more specific object is to provide an improved catheter construction which includes an ultrasonic transducer for use in laser angioplasty wherein the likelihood of accidental perforation of the arterial wall is reduced.

A further object of the invention is to provide a catheter construction including an ultrasonic transducer for use in laser angioplasty wherein ultrasonic imaging can be achieved with a minimum number of wires, possibly none, thereby reducing space requirements and simplifying the construction.

A still further object of the invention is to provide an ultrasonic imaging system for use in laser angioplasty which has a low space requirement and is easier to install in the catheter.

SUMMARY OF THE INVENTION

In accordance with the invention, a catheter for use in removing diseased tissue, such as atherosclerotic plaque deposits, comprises at least one optical fiber extending the length of the catheter for transmitting laser pulses, a transducer mounted at the distal end of the catheter and adapted to transmit ultrasonic energy in a direction generally radial of the catheter when irradiated by laser energy transmitted through said fiber, and means for detecting the acoustical energy reflected from tissue interfaces on which the ultrasonic energy impinges.

Range information is generated by the detecting means based on the time of arrival of the reflected ultrasonic pulses which represent, in known fashion, the distance from the catheter to the tissue interfaces. This provides a reliable indicator of the thickness of the arterial wall and, secondarily, the presence of atherosclerotic plaque. Armed with this information, an operator is less likely to direct the high power laser energy at a dangerously thin area of the arterial wall.

The invention contemplates various detection means including both electrical and optical means for producing information indicative of the ultrasonic signals reflected from the tissues surrounding the catheter tip.

THE DRAWINGS

FIG. 1 is a side cross-sectional view showing a catheter construction in accordance with a first embodiment of the invention;

FIG. 2 is a side cross-sectional view similar to FIG. 1 showing a catheter construction in accordance with a second embodiment of the invention;

FIG. 3 is a cross-sectional view along the line 3—3 of FIG. 1; and

FIG. 4 is a cross-sectional view along the line 4—4 of FIG. 1.

The principles of the invention can be employed to ablate atherosclerotic plaque or other types of diseased tissues such as cancerous growths. In its currently preferred embodiment, the invention is intended to be used for the ablation of atherosclerotic plaque; accordingly, the description of the preferred embodiment is directed to laser angioplasty.

FIG. 1, for purposes of explanation, shows an occlusion caused by an atherosclerotic plaque deposit 10 within blood vessel (artery) 12. A catheter 14 in the form of an elongated, flexible tube is dimensioned so that it can be inserted and advanced through a patient's coronary artery. Catheter 14 has a central through lumen so that it can be guided over a standard guide wire (not shown) in conventional fashion.

The catheter 14 comprises an inner core 16 and a shaft 18 which may include, for example, seven lumens 20. In a preferred embodiment, optical fibers 22 are positioned in respective ones of the lumens 20. The distal ends of the optical fibers 22 are retained in an annular holder 24 which is supported on the distal end of the core.

The two part catheter construction is used to facilitate the introduction of the optical fibers 22 and the electrical wires (described below) into the wall of the catheter. For enhanced flexibility, the shaft 14 and core 16 should be able to slide with respect to each other and the fibers 22 should be loose within the lumens 20.

An ultrasonic transducer in the form of a metal cap 26 having a conical proximal surface 27 is supported on a transparent collar 28 at the distal tip of the catheter. The collar 28 is made of a transparent material (for example artificial sapphire or fused silica) and thus functions as a window so that the laser energy transmitted through any one of the optical fibers 22 will impinge on the conical surface 27 of the metallic cap 26. Cap 26 is made of a metal such as aluminum or other metal such as gold which has the capability of producing ultrasonic energy when struck by a pulse of laser energy.

The ultrasonic energy produced by transducer 26 results from rapid thermal stress in the metal element caused by a laser pulse. The ultrasonic frequency is inversely related to the duration of the pulse. Typical useful ultrasonic frequencies are in the range of 1-20 MHz. For example, using a nitrogen laser operating at a wavelength of 337 nanometers, a laser pulse duration in the order of 2 nanoseconds will result in a range of ultrasonic frequencies up to 500 MHz. In accordance with the invention, a broad spectrum of ultrasonic frequencies will be generated. The ultrasonic frequency determines the depth to which the acoustical energy will be propagated into the tissue and the measurement resolution. Depending on the results desired, a detector frequency or frequencies may be determined empirically. It is contemplated that a detector sensitive to 20 MHz frequency may be used to provide the range information and, consequently, the critical data on arterial wall thickness.

While the generation of the acoustical energy in response to a laser pulse is an important part of this invention, it is known in other applications that laser energy can be used to cause metallic transducers to generate ultrasonic pulses. See, for example, Scruby, "Some Applications of Laser Ultrasound", Ultrasonics, July, 1989, (Vol. 27) ; Wang et al. "CO$_2$ Laser-Generated Acoustic Wave in Aluminum," Journal of Applied Physics, Jul. 1, 1989 (Vol. 66); and Akhmanov et al. "Pulsed Laser Opto-Acoustics, Achievements and Perspective", Infrared Physics, (Vol. 29), No. 2-4, pages 815-838, 1989. Accordingly, a detailed description of the technique and manner in which the ultrasonic energy is generated is not included in this specification.

In the preferred embodiment of the invention, the conical surface 27 of the transducer 26 is oriented with respect to the circumferentially arrayed optical fibers 22 so that the ultrasonic energy is propagated generally in a perpendicular or radial direction (slightly proximally) with respect to the axis of the catheter. The angular (azimuthal) direction in which the ultrasonic energy is directed depends on which of the circumferentially arrayed fibers is used to energize the transducer 26. In effect, by sequentially energizing transducer 26 through the individual optical fibers 26 the entire blood vessel can be scanned. This is beneficial as compared to some types of ultrasound scanning devices wherein the transducer must be rotated to cover a circumferential area. In place of the single conical surface 27, individual metallic members suitably oriented with respect to the respective optical fibers 22 may be used, or the surface may be segmented so that ultrasound is emitted only from the segment struck by the laser energy.

For diagnostic purposes, it is necessary to detect the ultrasonic energy reflected from the wall of the blood vessel. According to the embodiment illustrated in FIG. 1, a piezoelectric ultrasound transducer comprises a polyvinylidine fluoride (PVDF) film 32 coated on its inner and outer surfaces with gold layers 34 and 36, respectively. The gold layers 34 and 36 function as electrodes and are coupled to suitable electrical leads 38 which may be passed to the proximal end of the catheter through the walls of the catheter in the same fashion as the optical fibers 22 although, for purposes of clarity, the leads 38 are shown as passing through the central through lumen of the catheter. The transducer is wrapped around the holder 24 and can detect ultrasonic energy reflected from the blood vessel from any azimuthal direction.

The proximal end of the catheter may terminate in a connector 38 (shown schematically in FIG. 1) or other suitable device for enabling the catheter to be connected through a complementary connector 39 to a source of high power laser energy 42 or a source of low power laser energy 43. An optical switch 46 selectively connects high power laser 42 or low power laser 43 to the optical fibers 22 so that energy from either laser can be applied selectively to any desired one of the circumferentially arrayed fibers. The electrical leads 18 from the piezoelectric transducer 32 are coupled directly to the diagnostic equipment 44 to provide an appropriate indication of the tissue interfaces being irradiated by the ultrasonic energy from the cap 26.

In the illustrated embodiment, using seven optical fibers 22, instead of obtaining a true cross-section of the artery, a series of seven azimuthal "spikes" will be obtained. These "spikes" will indicate the range of the tissue interfaces scanned by a particular fiber thus providing the operator with an indication of at least the thickness of the arterial wall being scanned. To some extent, the ultrasonic information from the various fibers may also provide an indication of the presence of plaque although the main purpose of the ultrasonic scanning is to avoid perforation of the artery as opposed to recognizing the presence of plaque. The invention contemplates any possible use of the information obtained from the ultrasonic scan in accordance with the invention.

Various techniques are known for diagnosing blood vessels in order to detect the presence of plaque deposits and this invention does not depend on any particular diagnostic technique. If the ultrasonic scan provides useful information on the presence of plaque deposits, a particular response characteristic can be determined by appropriate experiments so that an operator can determine whether the signals appearing on leads 18, as analyzed by the diagnostic equipment 44, indicate that the portion of the blood vessel on which the ultrasonic energy is impinging constitutes plaque or not.

If the operator concludes that the blood vessel contains significant amounts of plaque, the laser 42 can be energized to convey a high energy laser output through any one of the optical fibers 22. Assuming that the ultrasonic energy from a particular fiber 22 has indicated that the arterial wall is thick enough so that the risk of perforation is minimal (and, possibly also, that the section of the artery being scanned contains plaque), by transmitting the high energy pulse through the same fiber, the operator is assured that the high energy laser pulse is being directed at the same section of the wall that the diagnostic procedure has indicated to be safe from perforation.

In known fashion, the high power laser energy can be applied until the plaque has been ablated. It is contemplated that the ablation and diagnostic procedures may alternate continuously with the lasers being appropriately controlled to cause first the generation of the ultrasound diagnostic pulses followed by the high power laser ablation pulses.

Although it is conceivable that a single laser may be used to generate both the ultrasonic diagnostic pulses and the high energy laser ablation pulses, in practice separate lasers are likely to be used because the pulse width required for ablation typically is too long to generate high frequency ultrasound. Where separate lasers are used, it is contemplated that suitable switching circuitry or dichroic elements of conventional design will be used to couple the laser energy to the appropriate fiber. By way of example only, the laser used to generate the ultrasound diagnostic pulses may have a wavelength of two nanoseconds, an energy level of one millijoule, and a pulse rate of fifty pulses per second. The laser used for ablation may be a Holmium YAG (Ho:YAG) laser with a wavelength of 2.1 micrometers, a pulse duration of 200 microseconds, an energy level of 100 millijoules to 1 joule, and a pulse rate of ten pulses per second.

FIG. 2 illustrates a second embodiment of the invention in which the diagnostic information is conveyed optically to the proximal end of the catheter. In FIG. 2, the collar comprises a stress birefringent crystal 48 (such as crystalline quartz) to detect the reflected ultrasonic energy. In all other respects, the construction of the device may be the same as that shown and described with respect to FIG. 1. As is well-known, a stress birefringent material rotates the polarization of the light passing through it in response to a stress applied to the material. In this case, the stress would be applied by the ultrasonic echoes from the walls of the blood vessel.

The distal end 52 of the transparent birefringent crystal 48 is coated with a material such as a conventional dielectric multilayer stack which transmits the laser pulse (for example, in the ultraviolet wavelength range) used to generate the ultrasonic energy. This coating reflects laser energy at a second laser wavelength (for example 631 nm He Ne laser) that may be used for the detection of the reflected ultrasonic energy. The low power laser 50 (for example, a Helium Neon laser) transmits continuous wave laser energy at this second wavelength through the selected optical fiber 22. The low power continuous wave laser energy is reflected by the coating on the surface 52 so that at least a portion of the continuous infrared laser energy is transmitted back through the selected fiber 22 to the proximal end of the catheter for diagnosis. Sufficient energy will be reflected from the side of the catheter and scattered back by the surrounding tissue to enable measurement of the reflected infrared laser energy although other modifications may be desirable to enhance the amount of energy reflected.

Where the optical detection system incorporates a stress birefringent crystal, the optical fibers 22 must each be of the type which preserves polarization. The amplitude of the reflected continuous wave infrared laser energy passing through the polarization preserving fiber 22 toward the proximal end of the catheter will therefore depend on the magnitude of the stress applied to the crystal 48 by the reflected ultrasonic energy from the blood vessel. This change in polarization can thus provide the means for diagnosing the character of the tissue irradiated by the ultrasonic energy from the transducer 26. In effect, the reflected laser energy from the continuous wave low power laser 50 is modulated by the stress applied to the crystal 48, which in turn depends on the nature and ranges to the interfaces from which the ultrasonic echoes are reflected.

In a third embodiment, also represented by the construction shown in FIG. 2, the optically transparent crystal 4; may comprise an acousto-optic material such as Lithium Niobate $LiNbO_3$. Such materials diffract or scatter light passing through them in response to the stress applied to the material by the reflected ultrasonic energy. In this case, it is not necessary that the fibers 22 be polarization preserving fibers since the diffraction of the laser energy in response to the stress applied to the crystal by the reflected ultrasonic energy will cause a change in amplitude of the reflected energy that can be analyzed for diagnostic purposes.

What is claimed is:

1. A catheter for use in removing diseased tissue within a body cavity, comprising
    an elongated tube having a distal end,
    an ultrasonic transducer at the distal end of said tube,
    means for transmitting laser energy through said catheter to said ultrasonic transducer to cause said transducer to transmit acoustical energy toward said tissue,
    means for detecting acoustical energy reflected rom said tissue, and
    means for transmitting laser energy through said catheter to ablate said tissue.

2. A catheter according to claim 1, wherein said detecting means comprises a piezoelectric transducer.

3. A catheter according to claim 1, wherein said detecting means comprises means for transmitting light through said catheter to said detecting means, and means for modulating such light depending on the acoustical energy reflected from the tissue on which the acoustic energy from said ultrasonic transducer impinges.

4. A catheter according to claim 3, wherein said modulating means comprises a birefringent crystal.

5. A catheter according to claim 3, wherein said modulating means comprises an acoustic-optic transducer for modulating light transmitted through said catheter and said acousto-optic transducer.

6. A catheter for use in removing atherosclerotic plaque deposits in a blood vessel, comprising
    an elongated, flexible tube adapted to be inserted into and advanced through said blood vessel,
    at least one optical fiber extending axially through said tube,
    an ultrasonic transducer in said catheter for transmitting acoustical energy toward a selected area of an inner surface of aid blood vessel having tissue interfaces in response to laser energy coupled through said optical fiber and impinging upon said transducer,
    detecting means responsive to ultrasonic energy reflected from said selected blood vessel area for producing a signal indicative of the tissue interfaces in said blood vessel area.

7. A catheter according to claim 6, wherein a plurality of optical fibers extend through said tube, laser energy transmitted through each of said optical fibers being adapted to cause said transducer to direct said acoustical energy toward a different selected area.

8. A catheter according to claim 7, wherein said detecting means comprises a piezoelectric transducer.

9. A catheter according to claim 7, wherein said detecting means comprises means for transmitting light through said catheter to said detecting means, and means for modulating such light depending on the ultrasonic energy reflected from the tissue on which acoustical energy from said ultrasonic transducer impinges.

10. A catheter according to claim 9, wherein said modulating means comprises a birefringent crystal and said optical fibers are polarization preserving fibers.

11. A catheter according to claim 9, wherein said modulating means comprises an acousto-optic transducer for modulating light transmitted through said optical fibers and said acousto-optic transducer.

12. Apparatus for use in diagnosing and removing atherosclerotic plaque deposits in a blood vessel, comprising
   a high power laser for ablating such plaque deposit,
   an elongated, flexible catheter adapted to be inserted into and advanced through said blood vessel,
   at least one optical fiber extending axially through said catheter,
   an ultrasonic transducer at the distal end of said catheter for transmitting acoustical energy toward a selected area of an inner surface of said blood vessel in response to laser energy coupled through said optical fiber and impinging upon aid transducer, said acoustical energy being directed generally radially of said catheter,
   detector means proximal of said ultrasonic transducer and responsive to ultrasonic energy reflected from said selected blood vessel area for producing a signal indicative of the thickness of said blood vessel in said selected area, and
   means for transmitting laser energy from said high power laser through said optical fiber to ablate plaque in said blood vessel area.

13. Apparatus according to claim 12, wherein a plurality of optical fibers extend axially through said catheter, the laser energy transmitted through said optical fibers being adapted to cause said transducer to direct said acoustical energy toward a different selected area, and wherein the laser energy transmitted to ablate plaque in said blood vessel area is transmitted through the same optical fiber through which laser energy was transmitted to said optoacoustic transducer.

14. Apparatus according to claim 13, wherein said detecting means comprises a piezoelectric transducer.

15. Apparatus according to claim 13, wherein said detecting means comprises means for transmitting light through one of said optical fibers to said detecting means, and means for modulating such light depending on the ultrasonic energy reflected from the tissue on which the acoustic energy from said optoacoustic transducer impinges.

16. Apparatus according to claim 15, wherein said modulating means comprises a birefringent crystal and said optical fibers are polarization preserving fibers.

17. Apparatus according to claim 15, wherein said modulating means comprises an acousto-optic transducer for modulating light transmitted through said optical fiber and said acousto-optic transducer.

18. A catheter for use in diagnosing tissue within a body cavity, comprising
   an elongated tube having a distal end and a proximal end,
   an ultrasonic transducer at the distal end of said tube,
   means for causing said transducer to transmit acoustical energy toward said tissue,
   means for transmitting light through said catheter to said proximal end, and
   means for modulating such light depending on the ultrasonic energy reflected from said tissue, said modulating means modulating such light to provide a signal at said proximal end which can be used to diagnose the character of said tissue.

19. A catheter according to claim 18, wherein said modulating means comprises a birefringent crystal and at least one polarization preserving optical fiber through which the light is transmitted.

20. A catheter according to claim 18, wherein said modulating means comprises an acousto-optic transducer for modulating light transmitted through said catheter and said acousto-optic transducer.

* * * * *